(12) United States Patent
Powers et al.

(10) Patent No.: US 7,186,990 B2
(45) Date of Patent: Mar. 6, 2007

(54) METHOD AND APPARATUS FOR DETECTING AND IMAGING THE PRESENCE OF BIOLOGICAL MATERIALS

(75) Inventors: Linda S. Powers, Logan, UT (US); Christopher R. Lloyd, Logan, UT (US)

(73) Assignee: Microbiosystems, Limited Partnership, Cheyenne, WY (US)

( * ) Notice: Subject to any disclaimer, the term of this patent is extended or adjusted under 35 U.S.C. 154(b) by 0 days.

(21) Appl. No.: 10/817,647

(22) Filed: Apr. 2, 2004

(65) Prior Publication Data

US 2004/0197771 A1    Oct. 7, 2004

Related U.S. Application Data

(63) Continuation-in-part of application No. 10/054,419, filed on Jan. 22, 2002, now Pat. No. 6,750,006.

(51) Int. Cl.
*G01N 21/64* (2006.01)
*C12Q 1/00* (2006.01)

(52) U.S. Cl. .............. 250/461.1; 250/458.1; 250/459.1; 435/4

(58) Field of Classification Search ............ None
See application file for complete search history.

(56) References Cited

U.S. PATENT DOCUMENTS

| | | |
|---|---|---|
| 3,850,525 A | 11/1974 | Kaye |
| 4,745,285 A | 5/1988 | Recktenwald et al. |
| 4,900,934 A | 2/1990 | Peeters et al. |
| 5,208,651 A | 5/1993 | Buican |
| 5,294,799 A | 3/1994 | Aslund et al. |
| 5,418,371 A | 5/1995 | Aslund et al. |
| 5,424,959 A | 6/1995 | Reyes et al. |
| 5,474,910 A | 12/1995 | Alfano |
| 5,491,343 A | 2/1996 | Brooker |
| 5,701,012 A | 12/1997 | Ho |
| 5,760,406 A | 6/1998 | Powers |
| 5,866,430 A | 2/1999 | Grow |
| 5,968,766 A | 10/1999 | Powers |
| 6,124,597 A | 9/2000 | Shehada et al. |
| 6,139,800 A | 10/2000 | Chandler |

*Primary Examiner*—Sandra E. Saucier
*Assistant Examiner*—Lora E Barnhart
(74) *Attorney, Agent, or Firm*—Jones, Waldo, Holbrook & McDonough; K. S. Cornaby

(57) ABSTRACT

Method and apparatus for the detection of biological material on non-living surfaces in which samples are exposed to electromagnetic radiation of specific energies capable of exciting various intrinsic fluorophores, and these fluorophores emit fluorescence that can be measured. The signal from the background, scattered excitation light and reflected excitation light is removed from the fluorescence signals due to the intrinsic fluorophores from the biological material and the intensities of the signals from the intrinsic fluorophores are required to lie within expected ranges.

1 Claim, 2 Drawing Sheets

METHOD AND APPARATUS FOR DETECTING AND IMAGING THE PRESENCE OF BIOLOGICAL MATERIALS

CROSS-REFERENCE TO RELATED APPLICATIONS

This application is a continuation-in-part of U. S. patent application Ser. No. 10/054,419 filed Jan. 22, 2002, which is now U.S. Pat. No. 6,750,006.

FIELD OF THE INVENTION

This invention relates to a method and apparatus for sensing, discerning among and imaging the presence of biological material (blood, semen, urine, saliva, sputum, etc.) on surfaces.

BACKGROUND OF THE INVENTION

Intrinsic fluorescence is well suited for detection of biological materials due to its high sensitivity, real-time feedback, lack of sample contact, and the capability to quickly scan large areas. Furthermore, it requires no reagents that may destroy, change or contaminate samples. Since fluorescence emission intensity (the detected signal indicating the presence of biological material) is proportional to the excitation intensity, weak signals can be observed by using high-power illumination. (The area that can be examined is likewise determined by the power output of the excitation source.) Detection of biological materials is possible as there is a wide variety and high concentration of biological components that exhibit intrinsic fluorescence: NAD[P]H and other reduced pyridine nucleotides (RPN), lumazines, pterins, flavoproteins, and other secondary metabolites. Nucleic acid polymers (DNA/RNA), proteins and various lipids exhibit higher energy fluorescence, making these markers potentially useful for the detection of fingerprints. Fluorescent metabolic breakdown products are found in urine. The heme component of blood (fresh and oxidized), as well as dried semen, also displays unique fluorescence patterns. The difference in intrinsic fluorescence emission of biological materials can be differentiated. Since many biological materials exhibit similar or indistinguishable components, simultaneous excitation of a sample with multiple energies characteristic of the excitation for fluorescent components with the subsequent collection and detection of emitted, reflected and scattered light energies (both associated with and independent of the fluorophores, respectively) is fundamental for the detection of biological material on a surface by the method described herein.

The detection of biological materials on real world sample surfaces is made more reliable by the aforementioned method for two reasons. First, the simultaneous excitation of biological material by multiple excitation energies (or sequential excitation by single energies) and ensuing coincident detection of numerous fluorescence signals reduces the chance of interference, as the probability of an interference source duplicating the characteristics of numerous fluorophores is extremely small. Second, the relative quantities of the intrinsic metabolites, and thus of the resulting fluorescent signals, have been found to fall within biologically determined ranges. Analysis of the signals is achieved with a method capable of two things: (1) separating the detected fluorescent signals originating from any biological material present from interferences or background signals and/or scattered excitation signals, and (2) a requirement that the intensities of the signals from various fluorescent components fall within expected ranges. Thus, the basis for the detection of biological materials is comprised of the following steps: first, excitation of a sample either simultaneously with multiple excitation energies or sequential excitation of multiple excitation energies characteristic of intrinsic fluorophores of biological material; second, the subsequent collection of the numerous individual fluorescence signals (associated with the maxima and minima of the emissions of these excited fluorophores); and finally, analysis of the collected signals with a method capable of removing background fluorescence (signals not originating from fluorescent components of the biological material, reflected excitation light nor scattered excitation light), reflected excitation signals, and scattered excitation signals; and comparing the relative fluorescence signal magnitudes of the expected ranges.

Long-established technologies and methods used for biological material collection from surfaces involve direct sampling with swabs or tape and/or visualization after treatment with reagents. Often the reagents used to visualize latent biological material may destroy, change or contaminate the sample. Since this invention employs detection of multiple intrinsic fluorophores from biological material, coupled with an analysis of the relative amount of signals due to these fluorophores, it can not only determine the presence of biological material, but is also capable of differentiating between various types of biological material. The invention disclosed herein uses no reagents, requires no physical contact with the sample, and delivers 'real-time' results.

Methodologies for detection of specific forensic biological materials include the use of antibodies (U.S. Pat. No. 6,605,705), antibodies coupled with enzymes and substrates (U.S. Pat. No. 6,696,569), and antibodies in strip assays utilizing fluorescent dyes (U.S. Pat. No. 6,686,167). Other methodologies use fluorescence to visualize DNA, protein or other biological material after addition of dyes (U.S. Pat. No. 6,512,236). Light sources are used to illuminate and detect biological material via fluorescence with high power excitation sources (U.S. Pat. RE37,136) and with imaging methods (U.S. Pat. Nos. 6,392,238 and 6,636,701).

In allowed U.S. patent application Ser. No. 10/054,419 by Powers and Lloyd, which is incorporated herein by reference, there is disclosed a method and apparatus for the detection of microbes on non-living surfaces and samples in which samples are exposed to electromagnetic radiation of numerous specific energies capable of exciting fluorescence from various metabolites, cofactors and cellular and spore components. Thus, the microbial cells and spores to be sampled (and more specifically the excited metabolites, cofactors and other cellular, viral and/or spore components) contained therein emit fluorescence that can be measured. The collected fluorescence signals (associated with the minima and/or maxima of the signals emitted from the cellular/viral/spore components) are analyzed with a method capable of (1) removing any background or reflected/scattered excitation signal, and (2) comparing the relative fluorescent signals of metabolites, cofactors and spore components to known physiological ranges.

Whereas the aforementioned patent application by Powers and Lloyd depends upon simultaneous excitation of multiple microbial components, the present invention utilizes either simultaneous or sequential excitation of multiple fluorophores associated with biological materials coupled with an algorithm that subtracts the detected signals due to the scattered and/or reflected excitation energies. This difference in design and methodology makes the current invention better able to detect and discriminate between wider varieties of biological materials on non-living surfaces relative to other fluorescence methods. The current invention is superior in its detection of biological materials as the detection of multiple intrinsic fluorophores reduces the probability of false positive results due to background interferences. The detection of biological materials with the foregoing method and apparatus will have uses in crime scene evidence collection, sterilization verification, validation of cleaning procedures, food production and preparation safety, and emergency response teams tasked with the detection, decontamination and protection of public infrastructure facilities.

Law enforcement agencies and crime laboratories are severely limited in their ability to detect and identify biological samples at crime scenes and on evidence substrates (types of surfaces). Many agencies literally rely on sight or touch to confirm the presence of suspected biological evidence. The impact of these limitations is manifest in the following risk factors: valuable evidence samples are overlooked, worthless samples are collected and analyzed, viable evidence samples are contaminated, enhancement techniques destroy or alter evidence samples, hazardous samples are improperly collected and packaged, crime scene personnel come in physical contact with biological hazards, crime scene personnel are exposed to a hazardous environment, search and examination procedures are time consuming and agency and/or laboratory resources are wasted. Evidence response teams and first responders are also the first at risk because of frequent contact with scenes, victims, and other evidence that may contain biological fluids. These officers usually arrive at the crime scene when the evidence is least contaminated, yet they (1) lack the technology to locate suspected biological fluids, and (2) cannot capture images of fluids in their actual condition or at their original location. It is an object of this invention to provide a method and apparatus for use in the detection, identification and imaging of biological evidence.

It is yet another object of the invention to provide a method and apparatus for use in the detection of biological contamination on food preparation surfaces in which the fluorescence of biological material fluorescent components are excited by electromagnetic radiation to distinguish between the varieties of biological materials, allowing contamination on food preparation surfaces to be determined without contact with said surface.

It is accordingly an object of the invention to provide a method and apparatus that can be used in the validation of cleaning procedures. As a specific object of the invention, the method and apparatus can be used to find biological material contamination inexpensively and rapidly in, for example, health-care facilities, hotel rooms, and public buildings.

SUMMARY OF THE INVENTION

The concepts of the present invention reside in a method and apparatus for the detection of biological material in which samples are exposed to electromagnetic radiation of numerous specific energies capable of exciting fluorescence from various intrinsic fluorophores. Thus, the biological material to be sampled (and more specifically the excited fluorescent components) contained therein emit fluorescence that can be measured. The collected fluorescence signals (associated with the minima and/or maxima of the signals emitted from the biological material components) are analyzed with a method capable of (1) removing any background or reflected/scattered excitation signal, and (2) comparing the relative fluorescent signals of metabolites, cofactors and spore components to expected ranges.

Thus, the method and apparatus of the present invention provides an inexpensive and rapid way in which to scan surfaces to detect the presence of biological material without contact with the sample material. Being able to evaluate biological material on a surface without contact reduces the risk of introducing contamination of the sample and exposure of personnel.

In accordance with this form of the invention, it is frequently desirable to utilize light source(s) emitting electromagnetic radiation above 200 nm. In accordance with the present form of the invention, the light emitted by the light source is specific to, or filtered to pass therethrough, electromagnetic radiation of energies specific to excite NAD[P]H and other reduced pyridine nucleotides (RPN), lumazines, pterins, flavoproteins, nucleic acid polymers (DNA/RNA), proteins, various lipids, metabolic breakdown products in urine, the heme component of blood (fresh and oxidized), and fluorophores in semen and other biological fluids.

In accordance with another embodiment of the invention, it is possible, and sometimes desirable, to direct electromagnetic radiation of ultraviolet energies (wavelengths between 200 and 300 nm) at the sample. The ultraviolet light excites aromatic amino acids, lipid components and nucleic acids, some of which emission is self-absorbed by the sample sequentially by other fluorescent metabolites in the 300 to 500 nm range, some of which emission is self-absorbed by the sample in turn exciting yet other fluorescent metabolites in the 500 to 800 nm range, part of which emission is used to further excite other components. The fluorescent emissions of the sample are collected and analyzed as described previously. The use of ultraviolet light results in a relatively shallow sampling penetration depth of a sample.

In accordance with another embodiment of the invention, it is possible, and sometimes desirable, to direct electromagnetic radiation of energies capable of exciting specific fluorescent biological components and also energies that do not interact with the biological fluorophores, biological material and/or the substrate material on which the sample is found. Thus, in accordance with this embodiment of the invention, the resulting fluorescent signal emanating from the sample (both from the biological components and those simply reflected and/or scattered from the surface) can be measured and the presence of a specific biological material determined by comparing the ratios of the emitted signals from the microbes compared to those reflected and/or scattered from the substrate.

In accordance with the practice of the invention, a sensor is used to detect not only the fluorescence generated by the intrinsic fluorophores but also to detect the reflected and/or scattered electromagnetic radiation. This serves to normalize the signal and compensate for variations in the signal that might otherwise be caused by the use of varying distances between a probe and the sample being scanned and variations between different samples or surfaces.

It has also been found that by rapidly changing the electromagnetic radiation directed to the sample at frequencies different than 60 Hertz, the effects of ambient light (and particularly fluorescent light) can be substantially minimized. The modulation of the excitation energy also permits the sensor to be moved to direct the electromagnetic radiation to various parts of a sample without substantially affecting the ability to detect biological material on a variety of surfaces.

Lasers and alternate light sources have been moderately successful at locating potential evidence fluids at crime scenes. Published reviews including Watkin, J. E., Wilkinson, D. A. "A Comparison of the Forensic Light Sources, Polilight, Luma-Lite, and Spectrum 9000," Journal of Forensic Identification, Vol. 44, No. 6, 1994, p. 632 and Auvdel, M. J., "Comparison of Laser and High Intensity Quartz Arc Tubes in the Detection of Body Secretions," Journal of Forensic Identification, Vol. 33, No. 4, 1988, pp. 929–945 describe the use of single wavelength fluorescence to detect some biological materials on selected substrates. However, these technologies have limitations. Many light sources have special power and support requirements, and some sources cannot be transported to remote crime scenes. Additionally, agencies that actually have portable laser or alternate light source technologies are restricted by instrument wavelengths that cannot differentiate evidence samples from common substances that also fluoresce (since the fluorescence of many biological materials is difficult to distinguish from the background). A method and apparatus that could identify potential evidence would help evidence response teams and first responders establish a viable perimeter, gather useful and uncontaminated evidence, and reduce hazardous exposure. This method and apparatus require no reagents, no contact with the sample, are inexpensive to perform and deliver 'real-time' results. These, and other objects, features and advantages of the present invention will become apparent upon review of the following detailed descriptions of the disclosed embodiments and the appended claims.

DETAILED DESCRIPTION OF THE INVENTION

Figure 1:
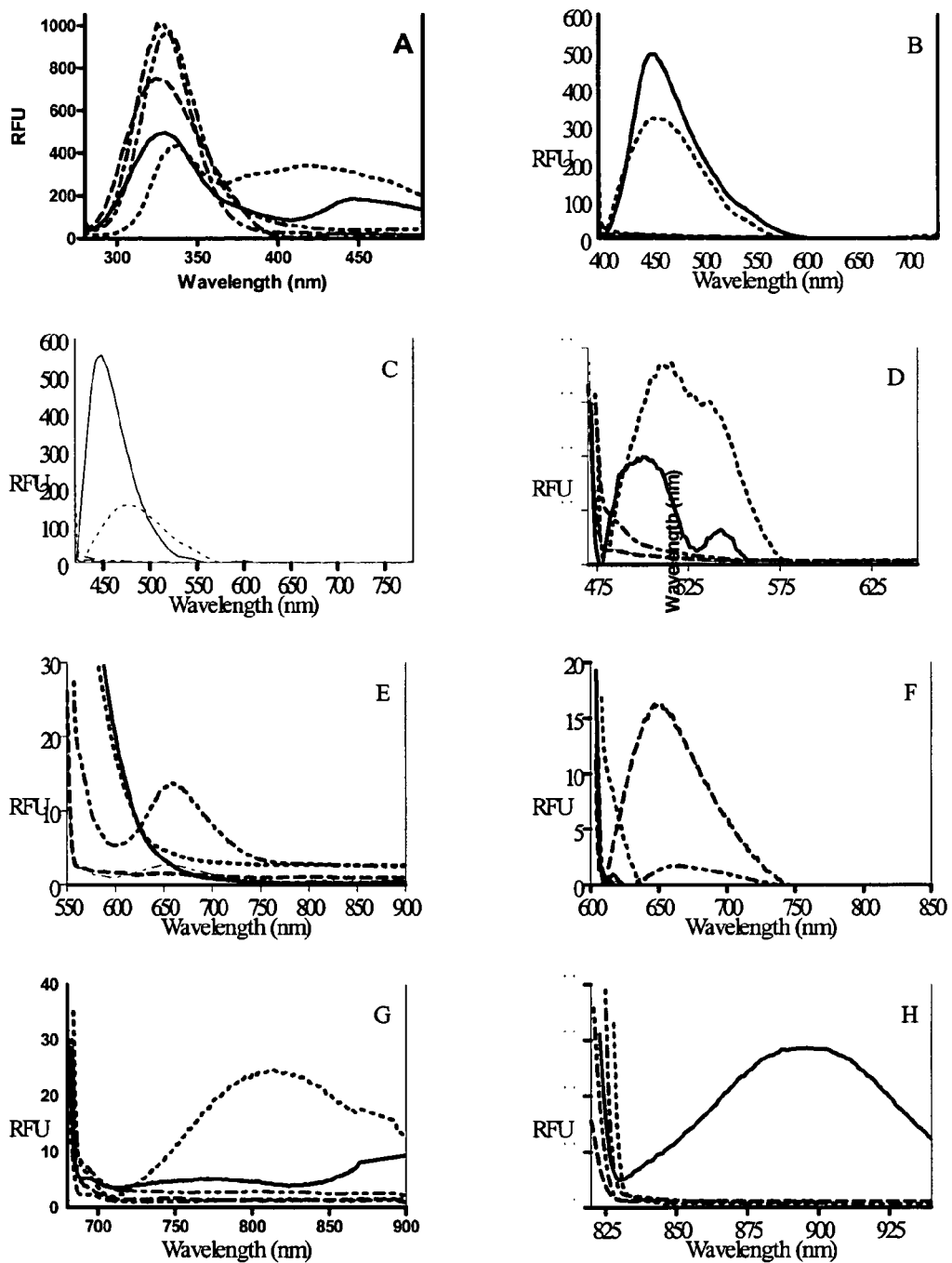
FIG. 1 shows the emission spectra of semen (———), skin oil (—·—··), blood (- - -) saliva (—•—•) and urine (·····) due to the various intrinsic fluorophores excited at 260 nm (A), 375 nm (B), 400 nm (C), 450 nm (D), 530 nm (E), 580 nm (F), 660 nm (G) and 800 nm (H).

An apparatus that can be used to apply the invention consists of a light source, excitation filters (if needed), focusing optics, imaging optics (if desired), emission filters and detectors. Electromagnetic radiation is directed from the light source towards the sample, passing through the excitation filters (if needed) and focusing optics (if necessary), to excite the intrinsic fluorophores in the sample. The scattered and reflected excitation radiation, along with the emitted fluorescence radiation, are collected and directed towards the detectors. Emission filters ensure that only the energy ranges of interest are measured.

Various embodiments of the invention, including different configurations and utilizing diverse components, are possible. The fundamental components for this biological material detection method permit: the excitation of multiple intrinsic biological fluorophores, collection and detection of emitted and reflected and/or scattered light energies, and analysis of the detected signals with a method that is able to correct for background interferences and compare the relative signal strengths to expected parameters. The configuration and components employed in any apparatus using this method should be matched with the application requirements and expected interferences.

It is possible, and sometimes desirable, to utilize a light source that provides a broad band illumination. The kind of light source employed is influenced by its ability to produce electromagnetic radiation of the wavelengths required to excite the intrinsic microbial components of interest. Additionally, it is sometimes desirable to use a pulsed light source allowing measurement of the environmental background during the off cycle. The light sources that can be used include lamps with various bulbs (e.g., mercury, tungsten, deuterium, xenon), light emitting diodes (LEDs), and diode lasers specific for the required excitation energies. The kind of light source used depends upon the intensity of excitation radiation needed and detection limit required.

The excitation and emission filters used in the various embodiments of the invention include interference filters, rugate filters, impregnated glass, series of cutoff filters, gelatin filters, monochromaters, gratings and the like. The light cutoff characteristics of the emission filters used depend on how much of the scattered and reflected excitation radiation signal can be tolerated by the analysis method or what detection limit is required. If light sources having only the energies of interest are employed, the excitation filters may not be necessary; if the light source is collimated (such as a laser) then the focusing optic may not be required. (The purpose of the focusing optic (if needed) is to direct the excitation radiation to the sampling area or volume.) It is important to note that with multi-photon excitation it is possible to use light sources with energies less than the excitation energies for single photon excitation of the fluorophores of interest.

The purpose of the collection optics is to deliver the light emitted from the excited fluorophores and that scattered and reflected from the sample to the detectors. If imaging of the emission from the excited surface is desired, then lenses and/or filters compatible with imaging are preferentially employed. If interference filters are utilized to discriminate these emission energies, then the collected light needs to be collimated for these filters to work optimally. Fiberoptic cables can also be used to both deliver the excitation radiation to the sample and to collect the emitted radiation and direct it towards the detectors. It is possible, and sometimes desirable, to utilize polished metal reflective, sapphire, fused silica, quartz, $MgF_2$, and/or $CaF_2$ optical components as many optical components exhibit fluorescence in the ultraviolet and visible range.

The detectors are used to convert the emitted electromagnetic radiation into an electrical signal that can be measured. Numerous detectors, with different sensitivities, can be utilized in the embodiments of the invention: photomultiplier tubes (PMTs), avalanche photodiodes (APDs), pin diodes, CCDs, and the like. If imaging of the fluorescence signal is desired, then a CCD array may be employed for both detection and imaging. The detector chosen would depend upon the energy of the radiation to be detected, the strength of the emission signal, and the required detection limit of the apparatus.

The collected emission energies, having been converted to amplified electrical signals, are analyzed with a method capable of removing any background fluorescence and scattered excitation contributions. The choice of excitation and emission energies used in a specific embodiment depends upon the target biological material. Table I lists the excitation and emission ranges of some of the more abundant intrinsic fluorescent compounds found in various biological materials.

TABLE I

Excitation and Emission Ranges for Select Human Body Fluids.

| Excitation Range (nm) | Emission Range (nm) | Skin Oil | Semen | Blood | Urine | Saliva |
|---|---|---|---|---|---|---|
| 250–300 | 320–360 | X | X | X | X | X |
| 250–300 | 380–460 |   |   |   | X |   |
| 250–290 | 430–480 |   | X |   |   |   |
| 360–390 | 420–510 |   | X |   | X |   |
| 390–410 | 430–540 |   | X |   | X |   |
| 430–470 | 480–570 |   | X |   | X |   |
| 520–540 | 630–700 | w |   |   |   | w |
| 570–590 | 630–700 |   |   | X |   | X |
| 640–680 | 760–840 |   |   |   | X |   |
| 790–810 | 860–930 |   | X |   |   |   |

(In Table I, the 'X' symbol indicates the presence of this fluorescence signature;
the 'w' symbol indicates the presence of a weak fluorescence signature.
The emiision ranges of the 430–470 nm excitation consist of multiple overlapping emissions.)

(In Table I, the 'X' symbol indicates the presence of this fluorescence signature; the 'w' symbol indicates the presence of a weak fluorescence signature. The emission ranges of the 430–470 nm excitation consist of multiple overlapping emissions.)

FIG. 1 shows the emission spectra of semen, skin oil, blood, saliva and urine due to the various intrinsic fluorophores excited at 260 nm (A), 375 nm (B), 400 nm (C), 450 nm (D), 530 nm (E), 580 nm (F), 660 nm (G) and 800 nm (H). This figure illustrates the differences of the fluorescence signals (both in presence and relative signal strength) between various biological materials. The analysis method uses these differences to discriminate between these samples. The magnitudes of the detected and background-subtracted signals can be used to roughly quantitate the amount of materials on the sample.

In the one embodiment of the invention, the use of excitation sources around 375, 580 nm, 660 nm and 800 nm would allow for the detection of and discrimination between semen, blood, and urine. These sources would allow the excitation of reduced pyridine nucleotides, various flavins, heme cofactors and other intrinsic fluorophores. The selection of filters for the emission detection of the excited fluorophores would include those inclusive of 420–540 nm, 630–700 nm, 760–840 nm and 860–930 nm. Additionally, other emission filters that allow for the determination of the magnitude of the reflected/scattered background can be preferentially employed. Additionally, exciting sources around 405 nm would impart further information that can be used to detect and differentiate between these biological materials.

Figure 2:
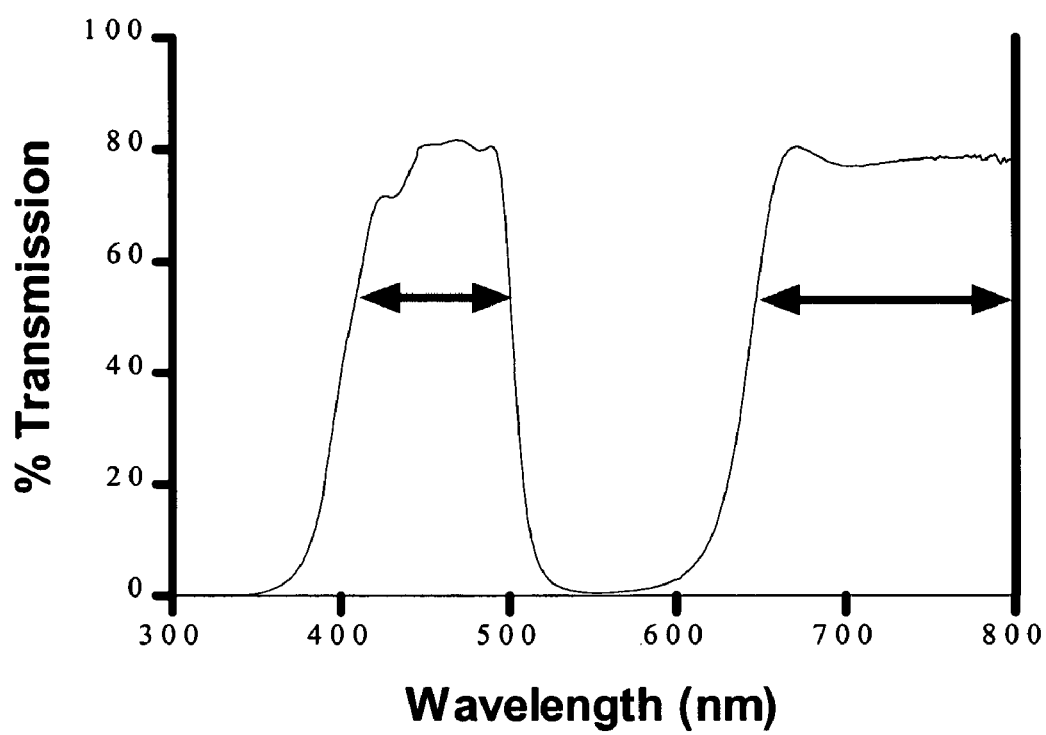
FIG. 2 shows the optical properties of an emission filter that can be used in an embodiment of the invention. The arrows indicate light wavelength ranges that can pass through the filter.

In another embodiment of the invention, emission filters with properties exemplified in FIG. 2 are employed. In this embodiment, emission filters are used that permit passage of emitted fluorescence in specific regions where emissions are expected, reject reflected excitation light, and permit higher energy light to pass for illumination of the substrate. As an example, the filter in FIG. 2 can used to detect semen by excitation of the surface with light at 290 nm; emission of intrinsic fluorophores in the semen occur between 430 and 480 nm (blue) and the red light that passes can be used to illuminate the substrate surface so the blue fluorescence (due to the semen) can be located easily. For clear differentiation between emitted intrinsic fluorescence and imaging of the substrate surface with higher wavelength light, the difference between the lowest energy intrinsic fluorescence emission and the highest energy substrate-imaging wavelength should be as large as possible. In practice, a difference of around 100 nm works well, but this difference should be at least 50 nm for visualization with the human eye.

The excitation energies may be directed at the sample simultaneously, in a corresponding manner or sequentially (if detection occurs on a faster timescale than movement of the instrument). Though Table I demonstrates that biological evidence can be detected and differentiated by the multi-wavelength fluorescence method described herein, other biological materials (including plant extracts, natural pharmaceuticals, nutrients, biominerals and the like) can be detected and identified in a like manner.

The embodiments of the present invention described above are intended to be merely exemplary, with other configurations, variations and modifications utilizing the fore mentioned basic ideas available to those skilled in the art without departing from the spirit of the invention. The scope of this method and apparatus to detect biological material includes utilization of simultaneous excitation of multiple intrinsic biological fluorophores, or sequential excitation of multiple intrinsic biological fluorophores by single excitation wavelengths, with subsequent analysis of the detected emissions with methods that concurrently account for background, scattered and reflected excitation signals and require said calculated reflected and scattered signal intensities and measured background signal intensities from the detected signals of the biological fluorescence signals to lie within expected ranges. All variations, modifications and configurations are intended to be within the scope of the present invention as defined in the appended claims.

What is claimed:

1. A method for distinguishing among intrinsically fluorescent biological materials on a surface at a crime scene, wherein said materials are selected from the group consisting of blood, saliva, semen, skin oil, and urine, said method comprising:

a) exciting at least one intrinsic fluorophore having a specific excitation range of electromagnetic radiation with a wavelength above 200 nm within said materials by exposing the materials to light with one or more ranges of excitation wavelengths;

b) detecting the signal intensities associated with the maxima and minima at one or more ranges of wavelengths of the resulting emission fluorescence;

c) detecting the background intensities at the minima and maxima of the fluorescence of the biological materials in the absence of excitation light and subtracting said background intensities from the signal intensities detected in step b);

d) calculating the intensities of the reflectance and scattering at the maxima of the fluorescence of the biological materials from the intensities of the background-subtracted minima;

e) subtracting the reflected and scattered signal intensities calculated in step d) and measured background intensities detected in step c) from the fluorescence of the biological materials detected in step b) at each of said one or more emission wavelengths, thereby determining the presence of a biological material by the presence of emitted fluorescence at particular emission wavelengths;

wherein the presence of blood is indicated by the emission of fluorescence in the 320–360 nm range upon excitation with excitation wavelengths in the 250–300 nm range and the emission of fluorescence in the 630–700 nm range upon excitation with excitation wavelengths in the 570–590 nm range; and the presence of saliva is indicated by the emission of fluorescence in the 320–260 nm range upon excitation with excitation wavelengths in the 250–300 nm range and the emission of fluorescence in the 630–700 nm range upon excitation with excitation wavelengths in the 520–540 nm range and 570–590 nm range; and the presence of semen is indicated by the emission of fluorescence in the 320–360 nm range upon excitation with excitation wavelengths in the 250–300 nm range; the the emission of fluorescence in the 430–480 nm range upon excitation with excitation wavelengths in the 250–290 nm range; the emission of fluorescence in the 420–510 nm range upon excitation with excitation wavelengths in the 360–390 nm range; the emission of fluorescence in the 430–540 nm range upon excitation with excitation wavelengths in the 390–410 nm range; the emission of fluorescence in the 480–570 nm range upon excitation with excitation wavelengths in the 430–470 nm range; and the emission of fluorescence in the 860–930 nm range upon excitation with excitation wavelengths in the 790–810 nm range;

the presence of skin oil is indicated by the emission of fluorescence in the 320–360 nm range upon excitation with excitation wavelengths in the 250–300 nm range; and the emission of fluorescence in the 630–700 nm range upon excitation with excitation wavelengths in the 520–540 nm range; and the presence of urine is indicated by the emission of fluorescence in the 320–360 nm range upon excitation with excitation wavelengths in the 250–300 nm range; the the emission of fluorescence in the 420–510 nm range upon excitation with excitation wavelengths in the 360–390 nm range; the emission of fluorescence in the 430–540 nm range upon excitation with excitation wavelengths in the 390–410 nm range; the emission of fluorescence in the 480–570 nm range upon excitation with excitation wavelengths in the 430–470 nm range; and the emission of fluorescence in the 760–840 nm range upon excitation with excitation wavelengths in the 640–680 nm range.

\* \* \* \* \*